(12) United States Patent
Kurimoto et al.

(10) Patent No.: US 8,038,182 B2
(45) Date of Patent: Oct. 18, 2011

(54) BREAKAGE RESISTANT FITTING

(75) Inventors: Munehito Kurimoto, Fukuroi (JP);
William A. Hagen, Canton, GA (US);
Michael R. Mahoney, Wentzville, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 148 days.

(21) Appl. No.: 12/374,059

(22) PCT Filed: Jul. 12, 2007

(86) PCT No.: PCT/US2007/015996
§ 371 (c)(1),
(2), (4) Date: Jan. 16, 2009

(87) PCT Pub. No.: WO2008/010958
PCT Pub. Date: Jan. 24, 2008

(65) Prior Publication Data
US 2009/0171322 A1    Jul. 2, 2009

Related U.S. Application Data

(60) Provisional application No. 60/831,823, filed on Jul. 18, 2006.

(51) Int. Cl.
*F16L 15/00* (2006.01)
(52) U.S. Cl. .......... 285/390; 285/332; 604/241
(58) Field of Classification Search .......... 285/332, 285/332.1, 334.5, 92, 401, 390; 604/905, 604/241, 533
See application file for complete search history.

(56) References Cited

U.S. PATENT DOCUMENTS

| | | | | |
|---|---|---|---|---|
| 2,454,557 | A | * | 11/1948 | Jacobson ............ 285/92 |
| 2,522,195 | A | * | 9/1950 | Richardson ............ 285/331 |
| 3,402,713 | A | * | 9/1968 | Senkowski et al. ...... 604/241 |
| 3,542,024 | A | * | 11/1970 | Burke ............ 604/241 |
| 4,237,882 | A |   | 12/1980 | Wickham |
| 4,266,815 | A | * | 5/1981 | Cross ............ 285/330 |
| 4,452,473 | A | * | 6/1984 | Ruschke ............ 604/241 |
| 4,735,441 | A | * | 4/1988 | Stephens ............ 285/148.19 |
| 5,702,374 | A | * | 12/1997 | Johnson ............ 604/533 |
| 6,436,075 | B1 |   | 8/2002 | Liao |
| 7,004,934 | B2 | * | 2/2006 | Vaillancourt ............ 604/533 |
| 7,618,072 | B2 | * | 11/2009 | Funamura et al. ...... 604/533 |
| 7,806,890 | B2 | * | 10/2010 | McKinnon et al. ...... 604/533 |
| 7,857,805 | B2 | * | 12/2010 | Raines ............ 604/533 |
| 2005/0090805 | A1 |   | 4/2005 | Shaw et al. |

FOREIGN PATENT DOCUMENTS

| | | |
|---|---|---|
| WO | WO 91/00750 | 1/1991 |
| WO | WO 2005/113038 | 12/2005 |

* cited by examiner

*Primary Examiner* — David E Bochna
(74) *Attorney, Agent, or Firm* — Marsh Fischmann & Breyfogle LLP

(57) ABSTRACT

An aspect of the invention, is directed to a luer fitting. The luer fitting may include a male luer, a luer collar disposed about the male luer, and a fulcrum disposed at a base portion of a receptacle between the male luer and the luer collar. Another aspect of the invention, is directed to a breakage resistant fitting. The breakage resistant fitting may include a male portion having a central fluid passage, a supplemental securement portion generally concentric with the male portion, and an annular receptacle between the male portion and the supplemental securement portion. The annular receptacle may include a base region having a mating clearance interspace sized substantially greater than a mating female fitting in a radial direction, or an axial direction, or a combination thereof.

26 Claims, 8 Drawing Sheets

BREAKAGE RESISTANT FITTING

CROSS-REFERENCE TO RELATED APPLICATION

This application claims priority to U.S. Provisional Patent Application No. 60/831,823 entitled "Breakage Resistant Fitting" filed on 18 Jul. 2006.

FIELD OF THE INVENTION

The invention relates generally to the field of medicine. Specifically, the invention relates to a durable or breakage resistant fitting for use with various medical devices, such as syringes, tubing, stopcocks, and fluid exchange devices.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

A variety of fittings or couplings are used to connect tubing, containers, syringes, and other devices in radiopharmacies, hospitals, and other healthcare facilities. Unfortunately, these fittings or couplings often break during usage, thereby spilling or wasting fluids passing through the particular fitting or coupling. For example, the fluid may include a patient's blood, a radiopharmaceutical, a contrast agent, or another drug being administered to the patient. One common source of breakage occurs between male and female fittings due to over tightening or over extending the fittings with respect to one another. For example, as a user couples the male and female fittings together, the user may extend the male and female fittings beyond a point of sufficient clearance resulting in compressive or tensile forces between the male and female fittings. Eventually, the over tightening or over extending between the male and female fittings can lead to critical forces or stress, which causes the male and/or female fitting to break. Again, this breakage can result in fluid spillage and delays in the particular medical procedure. For example, some medical procedures involve injecting a drug, contrast agent, or radiopharmaceutical at a particular physiological condition of a patient e.g., a specific heart rate. Thus, the forgoing breakage can detrimentally affect or delay the medical procedure, particularly in time sensitive medical procedures.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of features and aspects that may not be set forth below.

A first aspect of the invention relates to a luer fitting that includes a male luer and a luer collar disposed about the male luer. A receptacle is defined between the male luer and the luer collar. Further, a fulcrum is located toward a base portion of the receptacle.

A second aspect of the invention relates to a breakage resistant fitting. The breakage resistant fitting includes a male portion having a central fluid passage, a supplemental securement portion generally concentric with the male portion, and an annular receptacle between the male portion and the supplemental securement portion. The annular receptacle includes a base region having a mating clearance interspace sized substantially greater than a mating female fitting in a radial direction, or an axial direction, or a combination thereof.

In accordance with a third aspect of the present invention, there is provided a method that may include receiving a female luer about a male luer in a generally axial direction toward an abutment surface between the female luer and the male luer. The method also may include guiding an external portion of the female luer along a thread path in a structure surrounding the male luer. In addition, the method may include accommodating the external portion with clearance in one or more directions relative to the abutment surface between the male luer and the structure.

In accordance with a fourth aspect of the present invention, there is provided a method that may include connecting a breakage resistant fitting to a medical device for fluid transfer, wherein the breakage resistant fitting may include a first tubular member, a second tubular member disposed about the first tubular member, threads disposed between the first and second tubular members, and a recess disposed adjacent a fulcrum at a base portion between the first and second tubular members.

Various refinements exist of the features noted above in relation to the various aspects of the present invention. Further features may also be incorporated in these various aspects as well. These refinements and additional features may exist individually or in any combination. For instance, various features discussed below in relation to one or more of the illustrated embodiments may be incorporated into any of the above-described aspects of the present invention alone or in any combination. Again, the brief summary presented above is intended only to familiarize the reader with certain aspects and contexts of the present invention without limitation to the claimed subject matter.

BRIEF DESCRIPTION OF THE FIGURES

These and other features, aspects, and advantages of the present invention will become better understood when the following detailed description is read with reference to the accompanying figures in which like characters represent like parts throughout the figures, wherein.

DETAILED DESCRIPTION OF SPECIFIC EMBODIMENTS

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
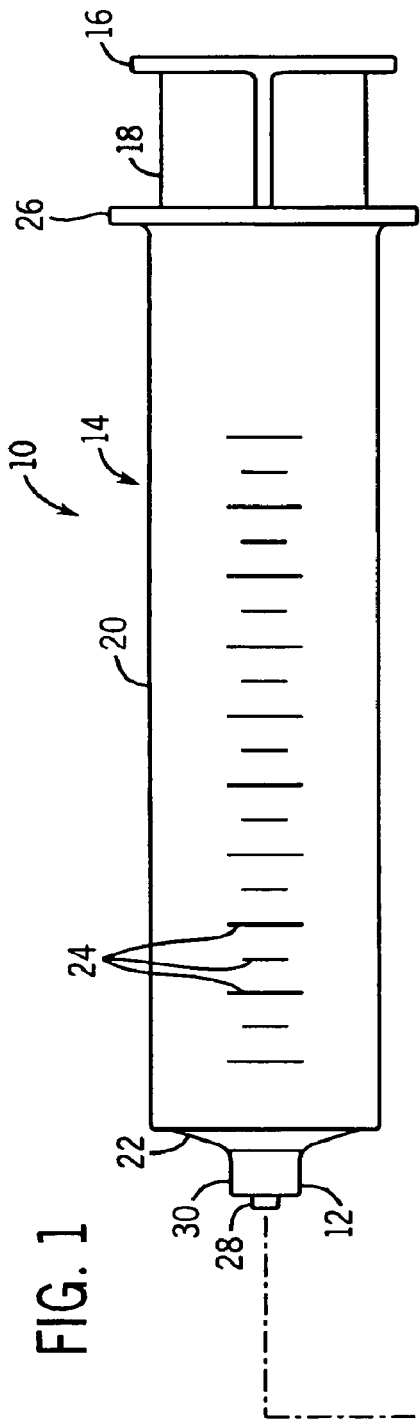
FIG. 1 is a top view of an exemplary embodiment of a system having a durable or breakage-resistant fitting disposed on a syringe.
Figure 1:
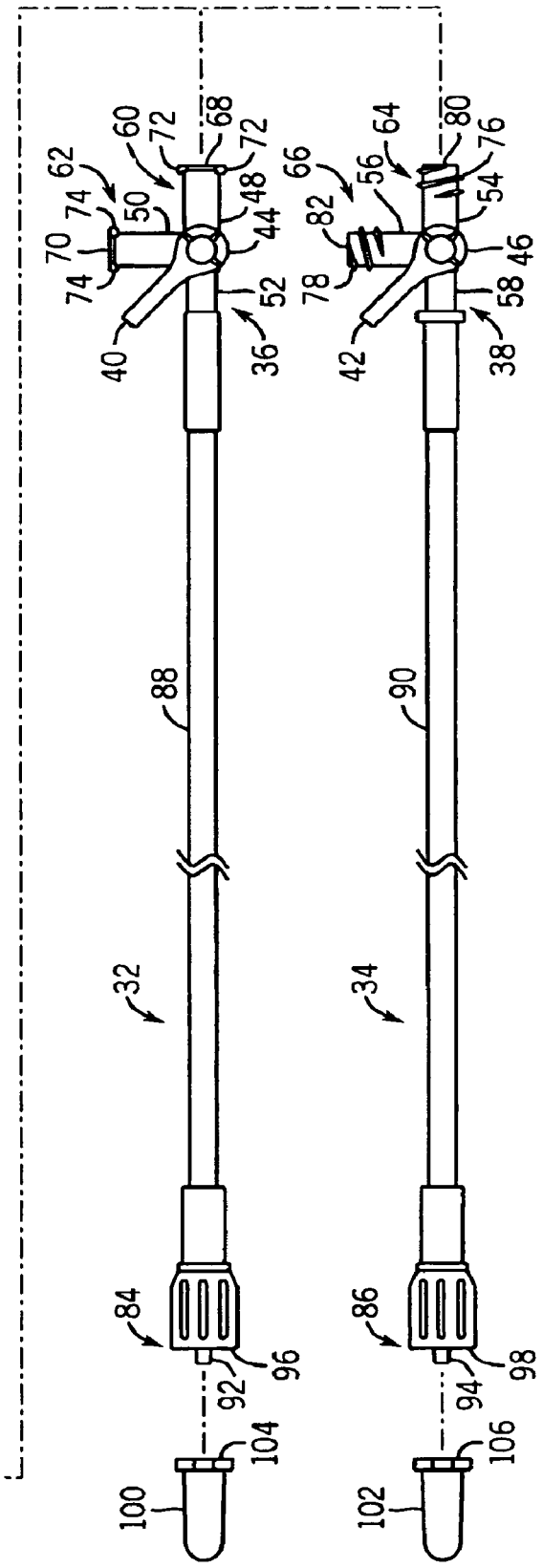

FIG. 1 is a top view of an exemplary embodiment of a syringe system 10 having one or more durable or breakage resistant fittings disposed on various medical devices. Specifically, the illustrated syringe system 10 includes a breakage resistant fitting 12 disposed on a syringe 14. The breakage resistant fitting 12 and/or the syringe 14 may be made from a variety of materials, such as plastic or glass. For example, the breakage resistant fitting 12 and/or the syringe 14 may be made from plastic materials, such as polycarbonate resin, polyethylene resin, polypropylene resin, acetyl resin, ABS resin, polymethylpentene resin or a generally transparent cyclic olefin copolymer. In some embodiments, the fitting 12 and/or the syringe 14 may be made from, or include, a radiation shielding material, such as lead, depleted uranium, tungsten impregnated plastic, and so forth. The illustrated syringe 14 may include a plunger 16 having a shaft 18 and a field plunger head disposed inside a syringe sleeve or barrel 20. In the illustrated embodiment, the breakage resistant fitting 12 may be disposed on a head 22 of the syringe sleeve or barrel 20, such that movement of the plunger 16 lengthwise along the syringe sleeve or barrel 20 forces a fluid to pass through the breakage resistant fitting 12. In addition, the syringe sleeve or barrel 20 may have a plurality of injection measurement indicia 24, such a volumetric marks extending crosswise on the syringe sleeve or barrel 20 one after the other between the head 22 and an opposite end 26 of the barrel 20. The breakage resistant fitting 12 may include a variety of connection features, such as a male portion 28 and a supplemental securement portion 30. In certain embodiments, the male portion 28 may include a male luer, and the supplemental securement portion 30 may include a luer collar disposed concentrically about the male luer. Thus, the breakage resistant fitting 12 may be generally described as a luer fitting or a male luer fitting. As discussed in further detail below, the breakage resistant fitting 12 includes one or more clearance, expansion, or general breakage resistant features to reduce the likelihood of breakage between the fitting 12 and a mating fitting, such as a mating fitting having a female luer.

As further illustrated in FIG. 1, the syringe system 10 may include alternative first and second fluid transmission systems 32, 34 having first and second stopcocks or valves 36, 38. The valves 36, 38 may include a two-way valve structure, a three-way valve structure, a four-way valve structure, or any other suitable arrangement of flow passages. For example, the valves 36, 38 may include valve levers 40, 42 moveably coupled to three-way valve bodies 44, 46. The illustrated valve levers 40, 42 may rotate 45 degrees, 90 degrees, 180 degrees, or another range of rotational movement to open and close various passages between different conduit portions of the three-way valve bodies 44, 46. For example, the three-way valve body 44 may include conduit portions 48, 50, 52. Similarly, the three-way valve body 46 may include conduit portions 54, 56, 58. As illustrated, the first valve 36 may include a first type or set of mating fittings 60, 62 disposed on the conduit portions 48, 50, whereas the second valve 38 may include a second type or set of mating fitting 64, 66 disposed on the conduit portions 54, 56.

Each of these mating fittings 60, 62, 64, 66 is configured to mate with the breakage resistant fitting 12 disposed on the syringe 14 with a greatly reduced likelihood of stress or breakage of the fitting 12 and/or the mating fittings 60, 62, 64, 66. The first mating fittings 60, 62 include female portions 68, 70 surrounded by external tabs or lugs 72, 74. In certain embodiments, the female portions 68, 70 may include female luers configured to mate concentrically around the male luer 28 of the breakage resistant fitting 12 disposed on the syringe 14 or another medical device. For example, the female portion 68, 70 may have a generally conical or tapered interface with the male luer 28 to enable a gradual compression fit between the female and male portions of the fittings. In addition, the lugs 72, 74 may be disposed on diametrically opposite sides of the ends of the conduit portions 48, 50. As discussed in further detail below, these opposite lugs 72, 74 may interface with the luer collar 30 of the breakage resistant fitting 12 during connection and disconnection between the fitting 12 and either the mating fitting 60 or the mating fitting 62. The threading of the luer coupling may exhibit any appropriate threading design. For instance, in some embodiments, the threading of the luer coupling may be characterized as a double right-hand screw.

In contrast, the second mating fittings 64, 66 may include external threads 76, 78 extending around the conduit portions 54, 56 in a spiral configuration. In other words, the external threads 76, 78 may spiral continuously around the circumference of the conduit portions 54, 56 to define a generally continuous spiral thread. In a similar manner, these external threads 76, 78 may engage with the luer collar 30 of the breakage resistant fitting 12 disposed on the syringe 14 or another medical device. In addition, the mating fittings 64, 66 may include female portions 80, 82 extending into the interior of the conduit portion 54, 56. Again, the female portions 80, 82 may have a generally conical or tapered interior surface, which can mate with and extend concentrically around the male luer 28 of the breakage resistant fitting 12. Thus, the lugs 72, 74 and the external threads 76, 78 are alternative types of supplemental mating securement portions configured to interface with the luer collar 30 in addition to the connection between the female portions 68, 70, 80, or 82 and the male luer 28.

In addition to the valves 36, 38, the fluid transmission systems 32, 34 may include first and second breakage resistant end fittings 84, 86. These end fittings 84, 86 may be coupled directly to the conduit portions 52, 58. In the illustrated embodiment, the end fittings 84, 86 may be coupled indirectly to the conduit portion 52, 58 via first and second lengths of tubing 88, 90. Similar to the fitting 12, the end fittings 84, 86 include male portions 92, 94 and supplemental securement portions 96, 98. Again, the male portions 92, 94 may include a male luer having a generally conical or tapered exterior surface. Moreover, the supplemental securement portions 96, 98 may include a luer collar or generally cylindrical structure disposed concentrically about the respective male portions 92, 94. In addition, the fluid transmission systems 32, 34 may include protective caps 100, 102 having female fittings 104, 106. For example, the female fittings 104, 106 may include a female luer having a generally conical or tapered interior surface configured to mate with a corresponding surface of the male luers 92, 94. Similar to the fitting 12 disposed on the syringe 14, the end fittings 84, 86 are configured to mate with various other female fittings with a reduced likelihood for breakage between the various female and male fittings.

Figure 2:
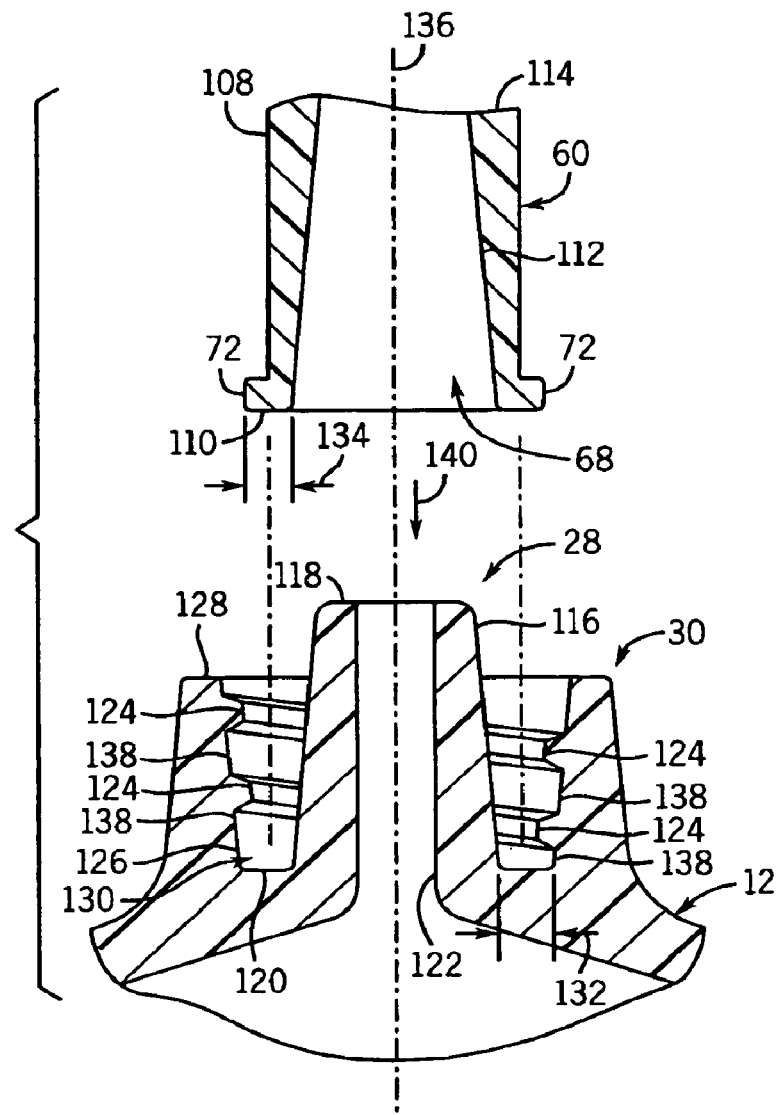
FIG. 2 is a partial cross-sectional view of an exemplary embodiment of a durable or breakage-resistant fitting exploded from a mating fitting.

FIG. 2 is a cross-sectional view of the breakage resistant fitting 12 exploded from the mating fitting 60 in accordance with an embodiment of the present technique. As noted above, the breakage resistant fitting 12 and the mating fitting 60 may be disposed on a variety of medical devices, such as syringes, conduits, stopcocks or valves, fluid transmission systems, radiopharmaceutical generators and equipment, powered or motorized injectors, and other suitable applications. In addition, the breakage resistant fitting 12 and the mating fitting 60 may be disposed on a variety of non-medical equipment and devices. Turning now to FIG. 2, the mating fitting 60 may include an elongated cylindrical body 108 extending lengthwise to a forward end 110 having the opposite lugs 72. The female portion 68, e.g., female luer, is generally disposed inside the elongated cylindrical body 108, and may include a generally conical or tapered inner surface 112 that gradually decreases in diameter from the forward end 110 toward a rearward portion 114 of the elongated cylindrical body 108. In other words, the tapered inner surface 112 converges inwardly at a small angle from the forward end 110 toward a point beyond the rearward portion 114.

Similarly, the male luer 28 of the breakage resistant fitting 12 may include a generally conical or tapered outer surface 116 configured to interface with the tapered inner surface 112 of the female luer 68 of the mating fitting 60. Specifically, the tapered outer surface 116 may increase in diameter from a tip 118 to a base 120 of the male luer 28. In other words, the outer surface 116 may generally diverge in a direction from the tip 118 toward the base 120. In addition, the male luer 28 may include a central fluid passage 122, such as a cylindrical shaped passage. As further illustrated in FIG. 2, the breakage resistant fitting 12 may include the luer collar 30 disposed concentrically about the male luer 28. For example, the luer collar 30 may have a generally cylindrical or conical shaped geometry.

In certain embodiments, the luer collar 30 may include one or more internal threads 124 configured to mate with the opposite lugs 72 disposed on the mating fitting 60. Alternatively, as discussed above, the internal threads 124 can mate with complete external threads, such as the external threads 76, 78 disposed on the mating fittings 64, 66 discussed above with reference to FIG. 1. In some embodiments, the internal threads 124 may extend around a generally conical or tapered inner surface 126 between the base 120 and an offset end 128 of the luer collar 30. For example, the internal threads 124 may be arranged in a spiral configuration that converges in a direction from the offset end 128 toward the base 120. Moreover, the internal threads 124 may include a single continuous thread that spirals around the tapered inner surface 126 between the offset end 128 and the base 120, such that the internal thread 124 gradually approaches the tapered outer surface 116 of the male luer 28. In view of the internal threads 124, the fitting 12 may be described as a thread assisted compression fitting.

In the illustrated embodiment, the breakage resistant fitting 12 provides a mating clearance interspace 130 at the base 120 between the tapered outer surface 116 and the tapered inner surface 126. For example, the mating clearance interspace 130 may have an interspace width 132 which is greater than a thickness 134 between the tapered inner surface 112 and a periphery of the lug 72 of the mating fitting 60. Thus, the mating clearance interspace 130 may include a generally radial clearance or annular shaped clearance configured to reduce the likelihood of radial forces between the exterior (e.g., lugs 72) of the mating fitting 60 and the inner surface 126 of the fitting 12. In other words, the mating clearance interspace 130 may substantially reduce or entirely eliminate the possibility of compressive or tensile forces between the exterior (e.g., lugs 72) of the mating fitting 60 and the interior 126 of the fitting 12, thereby reducing the likelihood of any breakage of the fittings 12 and/or 60. As discussed in further detail below, the mating clearance interspace 130 may include clearance in one or more directions, including the radial direction, an axial direction, or combinations thereof.

In the illustrated embodiment of FIG. 2, the mating fitting 60 may be coupled to the breakage resistant fitting 12 by simultaneously extending the female luer 68 about the male luer 28 and rotatingly threading the opposite lugs 72 with the internal threads 124 of the luer collar 30. In other words, the luer collar 30 engages with the opposite lugs 72 to pull or drive the female luer 68 inwardly toward and about the male luer 28. Eventually, the female luer 68 may compressively fit or extend around the male luer 28 at or near the base 120 of the breakage resistant fitting 12. For example, the mating fitting 60 may be rotated about a centerline or rotational axis 136 of the breakage resistant fitting 12, such that the opposite lugs 72 travel along a downwardly spiraling groove 138 between the internal threads 124. Thus, as a result of this downwardly spiraling path, the threads 124 impart a downward force 140 on the lugs 72. This downward force 140 may facilitate a compressive force or fit of the tapered inner surface 112 about the tapered outer surface 116 as the opposite lugs 72 approach and eventually reach the base 120 of the breakage resistant fitting 12. Although this mating between the fittings 12, 60 creates a compressive fit between the inner surface 112 of the fitting 60 and the outer surface 116, the mating clearance interspace 130 substantially reduces or generally eliminates the possibility of any compressive or outward radial forces from the exterior (e.g., lugs 72) of the fitting 60 and the inner surface 126 of the luer collar 30. As such, the fittings 12, 60 may create a watertight or airtight seal, while generally not risking breakage during the tightening procedure between the lugs 72 and the threads 124.

Figure 3:
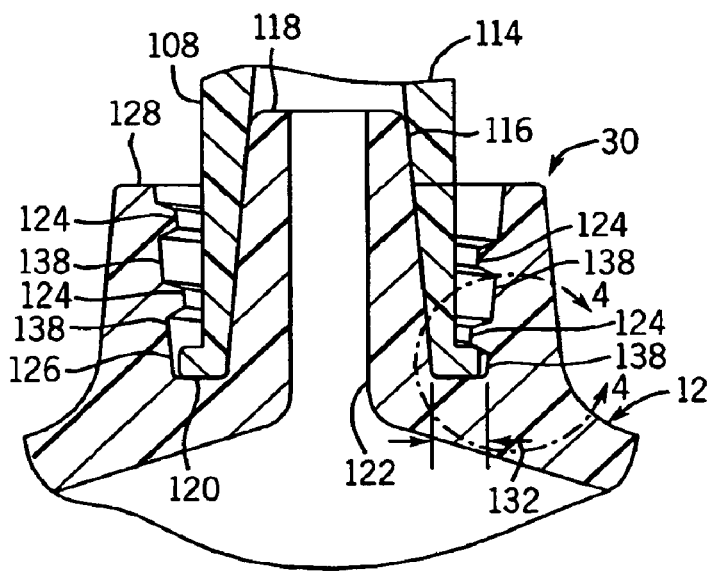
FIG. 3 is a partial cross-sectional view of the breakage-resistant fitting coupled to the mating fitting as illustrated in FIG. 2.

FIG. 3 is a cross-sectional view of the mating fitting 60 disposed in a secure position within the breakage resistant fitting 12. As illustrated, the mating clearance interspace 130 may generally ensure that the mating fitting 60, i.e., the opposite lugs 72, do not impart an outward radial force onto the luer collar 30, i.e., the tapered inner surface 126. As such, if the mating fitting 60 is threadingly driven all the way to the bottom surface or base 120, then the mating clearance interspace 130 reduces the likelihood or completely eliminates the possibility that the opposite lugs 72 will create an outward radial force and break the luer collar 30.

Figure 4:
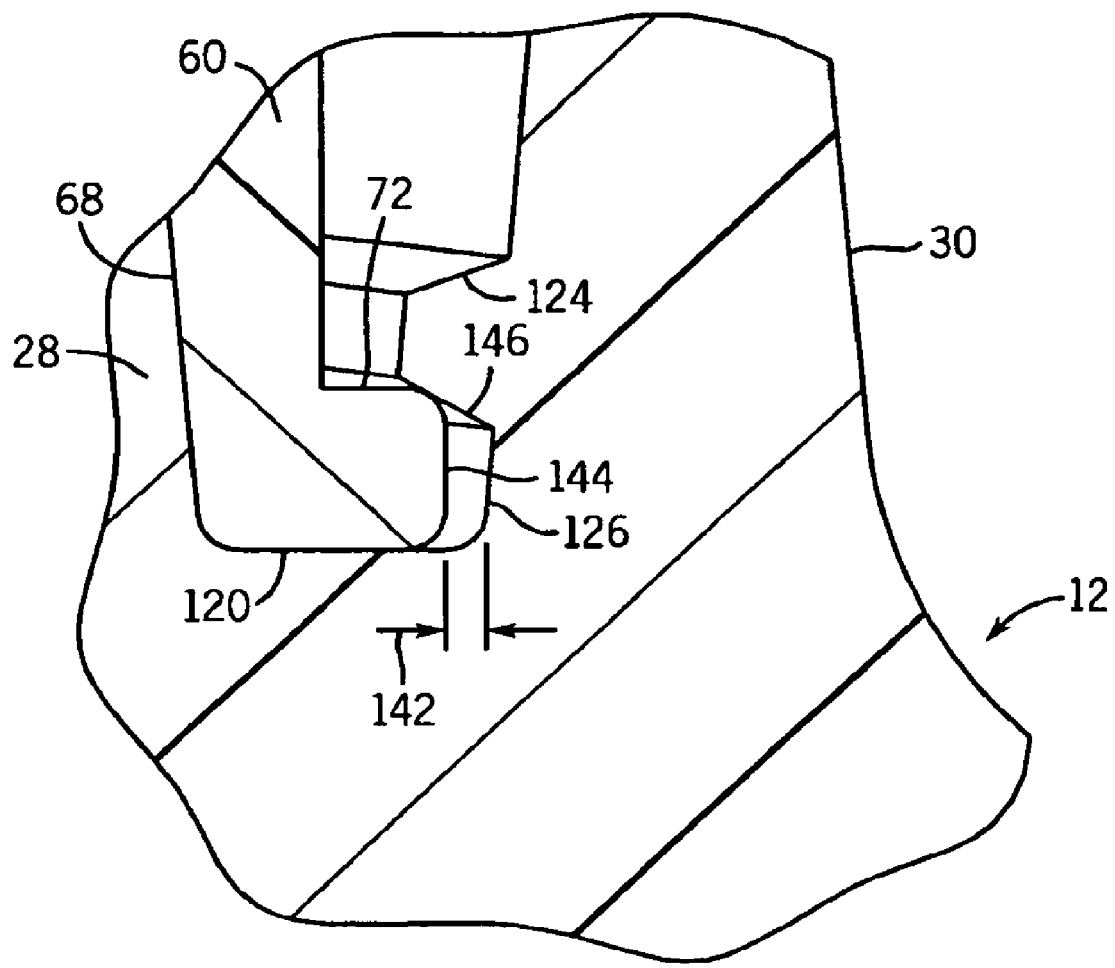
FIG. 4 is a partial cross-sectional view of an interface between the breakage resistant fitting and the mating fitting as illustrated in FIG. 3.

FIG. 4 is a partial cross-sectional view of the mating clearance interspace 130 with the mating fitting 60 fully engaged with the breakage resistant fitting 12 at the base 120 as illustrated in FIG. 3, further illustrating a clearance 142 between an outer periphery 144 of the lug 72 and the tapered inner surface 126 of the luer collar 30. The clearance 142 may be described as a radial clearance, a peripheral clearance, or an outer circumferential clearance relative to the outer periphery 144. As illustrated in FIG. 4, the lug 72 may deform under the last or final thread 124. In other words, the last thread 124 may force the lug 72 to compress between the base 120 and a lower side 146 of the thread 124. For this reason, other embodiments of the breakage resistance fitting 12 include additional space to accommodate the opposite lugs 72 below the lower side 146 of the internal threads 124.

Figure 5:
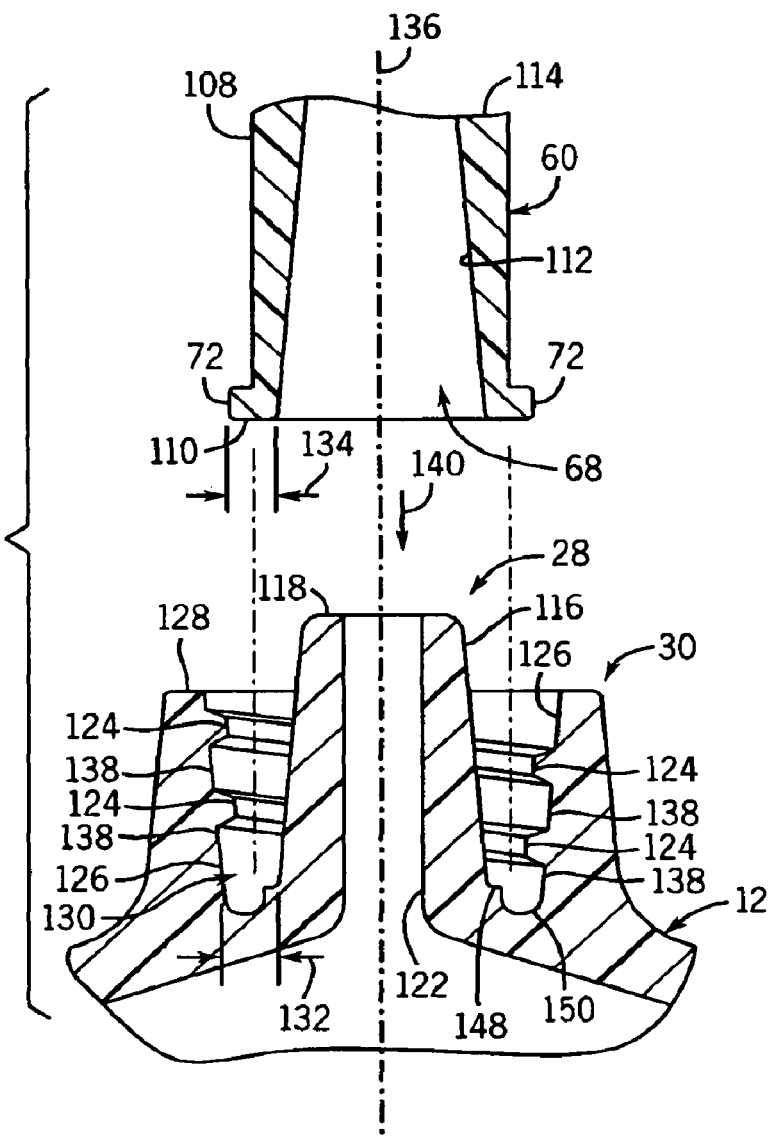
FIG. 5 is a partial cross-sectional view of another embodiment of a breakage resistant fitting exploded from a mating fitting.

FIG. 5 is a cross-sectional view of an alternative embodiment of the mating fitting 60 exploded from the breakage resistant fitting 12, wherein the base 120 of FIGS. 2-4 is replaced or modified to include a bottom stop or fulcrum 148 and a deformation channel or inward expansion groove 150 in the mating clearance interspace 130 between the tapered outer surface 116 and the inner surface 126. The fulcrum 148 may be defined as a rigid support or ridge about which the lug 72 of the mating fitting 60 pivots, bends, or generally deforms deeper into the inward expansion groove 150 as the mating fitting 60 is inserted into the breakage resistant fitting 12. In other words, the fulcrum 148 may be defined as a pivot point/region, a bending point/region, or a deformation point/region that cooperates with the internal threads 124 to leverage or force the lug 72 to curve downwardly into the inward expansion groove 150. The fulcrum 148 also may be defined as a pivoting inducement structure, a bending inducement structure, or a deforming inducement structure. In context of the present application, the element 148 is described as a fulcrum for simplicity, but the fulcrum 148 may include any of the definitions provided above.

In the illustrated embodiment, the fulcrum 148 may extend partially, intermittently, or entirely around the circumference of the male luer 28. For example, the fulcrum 148 may have a generally ring shaped, annular, or cylindrical geometry protruding outwardly from the tapered outer surface 116 of the male luer 28. However, the fulcrum 148 does not extend entirely from the tapered outer surface 116 to the opposite inner surface 126 of the luer collar 30. Again, the fulcrum 148 may be interrupted in between the surfaces 116, 126 by the inward expansion groove 150. In certain embodiments, the inward expansion groove 150 may extend partially, intermittently, or entirely around the circumference of the male luer 28 between the fulcrum 148 and the tapered inner surface 126. For example, the inward expansion groove 150 may have a generally ring shaped or annular geometry, which extends axially deeper than the fulcrum 148 into the luer pocket between the male luer 28 and the luer collar 30.

Figure 6:
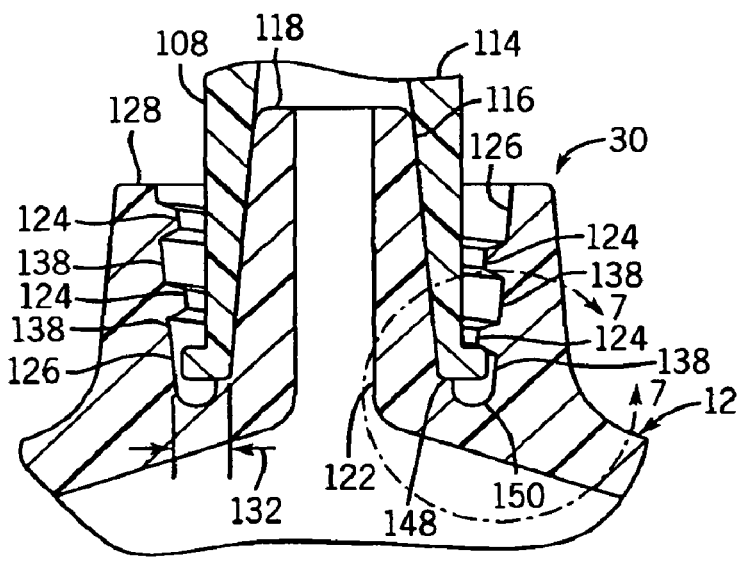
FIG. 6 is a partial cross-sectional view of the breakage resistant fitting coupled to the mating fitting as illustrated in FIG. 5.

Again, as discussed in detail above with reference to FIGS. 2 and 3, the mating fitting 60 may be coupled to the breakage resistant fitting 12 by simultaneously threading the opposite lugs 72 along the internal threads 124 and compressively fitting the female luer 68 about the male luer 28. Eventually, the internal threads 124 and corresponding downwardly spiraling groove 138 drive the opposite lugs 72 to engage or bottom out on the fulcrum 148. For example, FIG. 6 is a cross-sectional view of the mating fitting 60 coupled to the breakage resistance fitting 12 as illustrated in FIG. 5, further illustrating the opposite lugs 72 engaging the internal threads 124 in the mating clearance inner space 130. As illustrated in FIG. 6, the opposite lugs 72 may initially compressively conform between the internal threads 124 and the fulcrum 148 as discussed above with reference to FIG. 4. However, the inward expansion groove 150 may enable the opposite lugs 72 to deform or expand in a direction away from the internal threads 124 and into the groove 150. Again, the fulcrum 148 may cooperate with the internal threads 124 to leverage or force the lug 72 to pivot, bend, or deform downwardly into the inward expansion groove 150.

Figure 7:
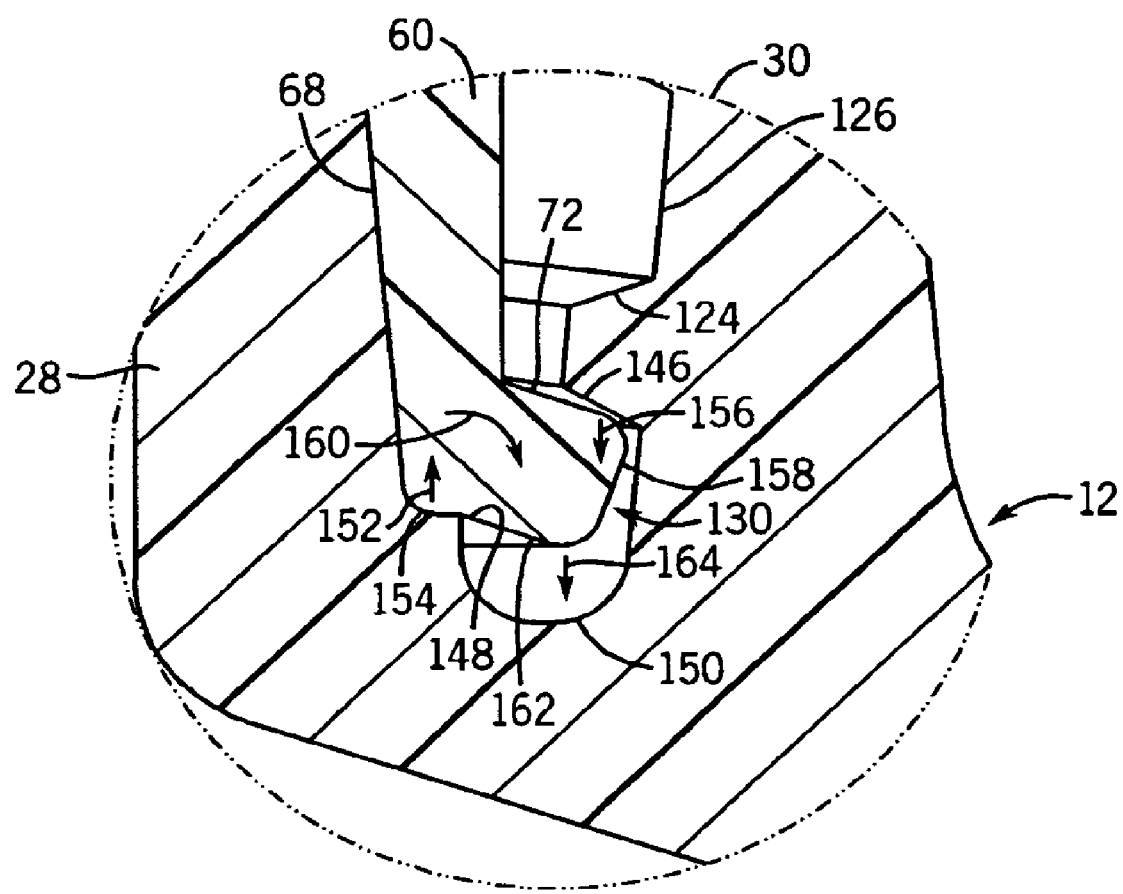
FIG. 7 is a partial cross-sectional view of an interface between the breakage resistant fitting and the mating fitting as illustrated in FIG. 6.

FIG. 7 is a partial cross-sectional view of the mating fitting 60 coupled to the breakage resistant fitting as illustrated in FIG. 6, further illustrating the deformation of the opposite lugs 72 in the mating clearance interspace 130. As illustrated, the fulcrum 148 may impart an upward force 152 on a lower interior portion 154 of the mating fitting 60, while the bottom surface 146 of the internal thread 124 imparts a downward force 156 on an upper peripheral portion 158 of the lug 72. As a result, these opposite upward and downward forces 152, 156 may create a rotational force or torque 160 in the lug 72, thereby forcing a substantial portion 162 of the lug 72 to deform or expand downwardly into the inward expansion groove 150 as illustrated by arrow 154. As such, the fulcrum 148 and the inward expansion groove 150 may cooperate with the bottom side 146 of the internal thread 124 to reduce the likelihood of breakage associated with forces between the internal thread 124 and the lug 72 as discussed above with reference to FIGS. 3 and 4. In addition, as discussed above with reference to FIGS. 2-4, the additional clearance 142 between the outer periphery of the lug 72 and the tapered inner surface 126 of the luer collar 30 may reduce the likelihood of radial forces and possible breakage between the mating fitting 60 and the breakage resistant fitting 12. As a result, the combination of the mating clearance interspace 130 having the clearance 142 along with the fulcrum 148 and the inward expansion groove 150 may substantially reduce the likelihood of critical stresses and breakage in either the axial or radial directions at the interfaces between the mating fitting 60 and the breakage resistance fitting 12.

Figure 8:
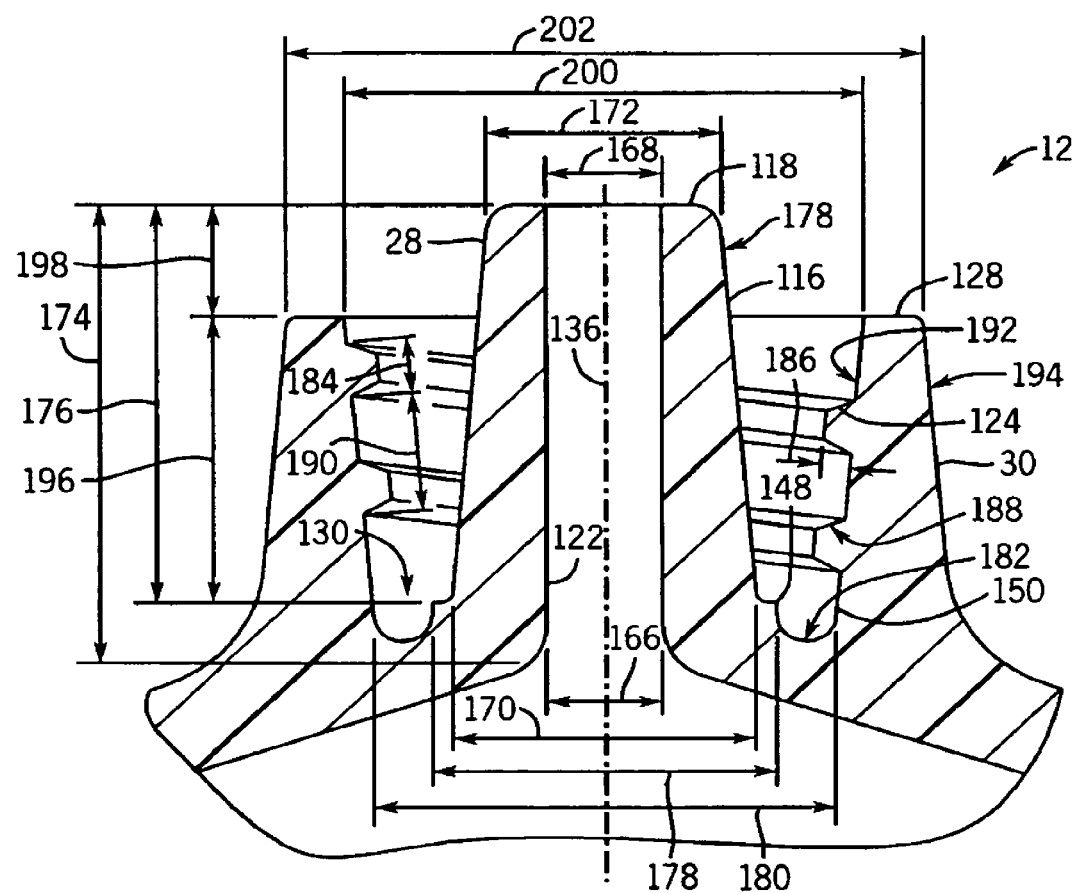
FIG. 8 is a cross-sectional view of the breakage resistant fitting as illustrated in FIGS. 5-7 illustrating exemplary dimensions.

FIG. 8 is a cross-sectional view of the breakage resistant fitting 12 as illustrated in FIGS. 5-7, further illustrating dimensions of the various components in accordance with one embodiment of the fitting 12. As illustrated, the central fluid passage 122 of the male luer 28 has an inner diameter 166 leading to an inner diameter 168 along the length of the passage 122. For example, these dimensions 166, 168 may be 1.932 mm and 1.8 mm. The male luer 28 also includes an outer diameter 170 leading to an outer diameter 172 lengthwise along the tapered outer surface 116. For example, the dimensions of the outer diameters 170, 172 may be 4.46 mm and 3.98 mm. In addition, the central fluid passage 122 may have a length 174, such as 10.49 mm. Moreover, the male luer 28 may have a length 176, such as 8.33 mm measured between the fulcrum 148 and the tip 118. Accordingly, the tapered outer surface 116 of the male luer 28 may have a taper angle 178, such as a 6/100 luer taper. Regarding the fulcrum 148 and the inward expansion groove 150, these features may have diameters 178, 180, such as 5.46 mm and 7.96 mm, relative to the centerline 136. Moreover, the inward expansion groove 150 may have a curvature radius 182, such as 0.6 mm. Regarding the luer collar 30, the internal threads 124 may have a width dimension 184, a thickness dimension 186, a taper dimension 188, and an interspacing dimension 190, such as 1 mm, 0.5 mm, 25 degrees (i.e., relative to a line perpendicular to the inner surface 126), and 2.5 mm, respectively. In addition, the luer collar 30 may have inner and outer taper dimensions 192, 194, such as 0.5 degrees and 1 degree relative to the centerline 136. The luer collar 30 also may have a length dimension 196, such as 6.03 mm, measured between the fulcrum 148 and the offset end 128. Furthermore, the offset end 128 may have a lengthwise offset distance 198, such as 2.3 mm, measured between the luer collar 30 and the tip 118 of the male luer 28. Furthermore, the offset end 128 of the luer collar 30 may have inner and outer diameters or dimensions 200, 202, such as 8.09 mm and 10.8 mm. In the illustrated embodiment of FIG. 8, the exemplary dimensions may have tolerances of plus/minus 0.12 mm for length, width, or other distances, while the angles may have tolerances of plus/minus 0.5 degrees. However, some of the exemplary dimensions may have more specific or tighter tolerances. For example, the thread dimensions 184, 186 may have tolerances of plus 0 mm or minus 0.05 mm. By further example, the outer diameter 172 of the male luer 28 may have a tolerance of plus 0 mm or minus 0.05 mm. In addition, the inner diameter 200 of the luer collar 30 may have a tolerance of plus 0.05 mm or minus 0 mm. The dimensions and tolerances discussed in detail above with reference to FIG. 8 are simply one embodiment of the breakage resistant fitting 12. Accordingly, a variety of other dimensions may be employed for the various portions of the breakage resistant fitting 12 in accordance with the various embodiments of the present technique.

In certain embodiments, the breakage resistant fitting 12 may be used along with the syringe 14, tubing, or other containers and fluid transmission systems. For example, the syringe 14 having the breakage resistant fitting 12 illustrated and described above with reference to FIGS. 1-9 may be filled or pre-filled with one or more medical fluids, such as contrast agents, radiopharmaceuticals, tagging agents, biocompatible flushes, bodily fluids (e.g., blood, urine, etc.), pharmaceuticals, or combinations thereof. Specifically, the medical fluid may include a contrast agent for medical imaging, such as magnetic resonance imaging (MRI), computed tomography (CT), radiography (e.g., x-ray), or ultrasound. Alternatively, the medical fluid may include a radioisotope or radiopharmaceutical for radiation-based treatment or medical imaging, such as positron emission tomography (PET) or single photon emission computed tomography (SPECT). The syringe 14 may be used to inject the medical fluid into a subject or patient.

Nuclear medicine utilizes radioactive material for diagnostic and therapeutic purposes by injecting a patient with a small dose of the radioactive material, which concentrates in certain organs or biological regions of the patient. Radioactive materials typically used for nuclear medicine include Technetium-99m, Indium-113m, and Strontium-87m among others. Some radioactive materials naturally concentrate toward a particular tissue, for example, iodine concentrates toward the thyroid. However, radioactive materials are often combined with a tagging or organ-seeking agent, which targets the radioactive material for the desired organ or biologic region of the patient. These radioactive materials alone or in combination with a tagging agent are typically referred to as radiopharmaceuticals in the field of nuclear medicine.

In certain embodiments, the subject may be scanned or generally imaged by a suitable medical diagnostic and/or imaging system, such as listed above. For example, after the contrast agent or radiopharmaceutical enters the blood stream and distributes or focuses on a particular organ or area of interest, the diagnostic and/or imaging system may function to acquire imaging data, process the data, and output one or more images. Thus, the diagnostic and/or imaging system may include detector/acquisition hardware and software, data/image processing hardware and software, data/image storage hardware and software, a display, a printer, a keyboard, a mouse, a computer workstation, a network, and other associated equipment. For example, at relatively lower doses of a radiopharmaceutical, a radiation imaging system (e.g., a gamma camera) provides an image of the organ or biological region that collects the radiopharmaceutical. Irregularities in the image are often indicative of a pathologic condition, such as cancer. Alternatively, higher doses of the radiopharmaceutical may be used to deliver a therapeutic dose of radiation directly to the pathologic tissue, such as cancer cells.

Figure 9:
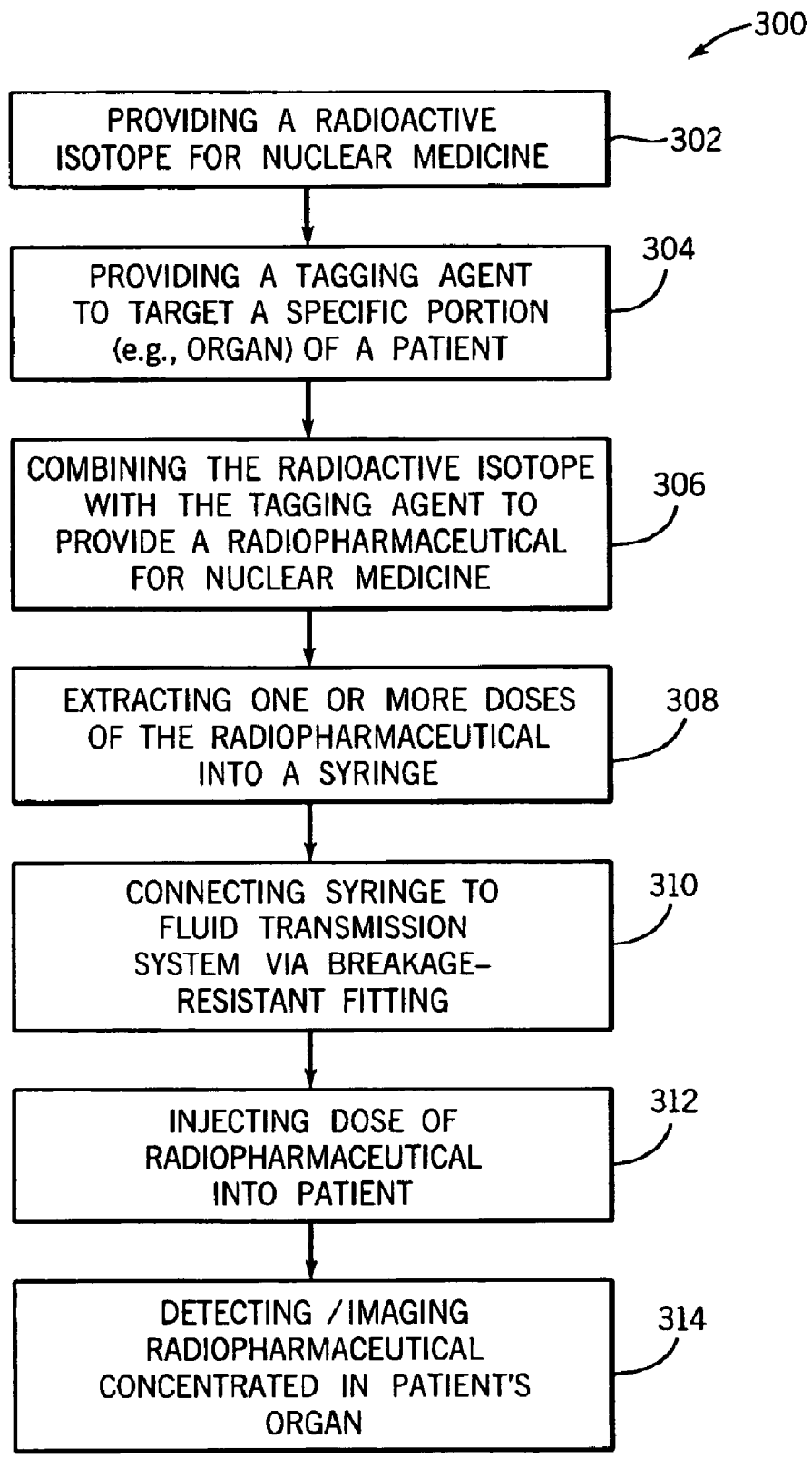
FIG. 9 is a flowchart illustrating an embodiment of a nuclear medicine process utilizing one or more of the syringes having a breakage resistant fitting as illustrated in FIGS. 1-8.

FIG. 9 is a flowchart illustrating an exemplary nuclear medicine process utilizing the breakage resistant fitting 12 and the syringe 14 illustrated with reference to FIGS. 1-8. As illustrated, the process 300 begins by providing a radioactive isotope for nuclear medicine at block 302. For example, block 302 may include eluting technetium-99m from a radioisotope generator. At block 304, the process 300 proceeds by providing a tagging agent (e.g., an epitope or other appropriate biological directing moiety) adapted to target the radioisotope for a specific portion, e.g., an organ, of a patient. At block 306, the process 300 then proceeds by combining the radioactive isotope with the tagging agent to provide a radiopharmaceutical for nuclear medicine. In certain embodiments, the radioactive isotope may have natural tendencies to concentrate toward a particular organ or tissue and, thus, the radioactive isotope may be characterized as a radiopharmaceutical without adding any supplemental tagging agent. At block 308, the process 300 then may proceed by extracting one or more doses of the radiopharmaceutical into a syringe or another container, such as a container suitable for administering the radiopharmaceutical to a patient in a nuclear medicine facility or hospital. The process 300 then proceeds by connecting the syringe to a fluid transmission system via a breakage resistant fitting (block 310). For example, the breakage resistant fitting 12 may be disposed on the syringe 14 as discussed above. At block 312, the process 300 proceeds by injecting or generally administering a dose of the radiopharmaceutical into a patient. After a pre-selected time, the process 300 proceeds by detecting/imaging the radiopharmaceutical tagged to the patient's organ or tissue (block 314). For example, block 314 may include using a gamma camera or other radiographic imaging device to detect the radiopharmaceutical disposed on or in or bound to tissue of a brain, a heart, a liver, a tumor, a cancerous tissue, or various other organs or diseased tissue.

Figure 10:
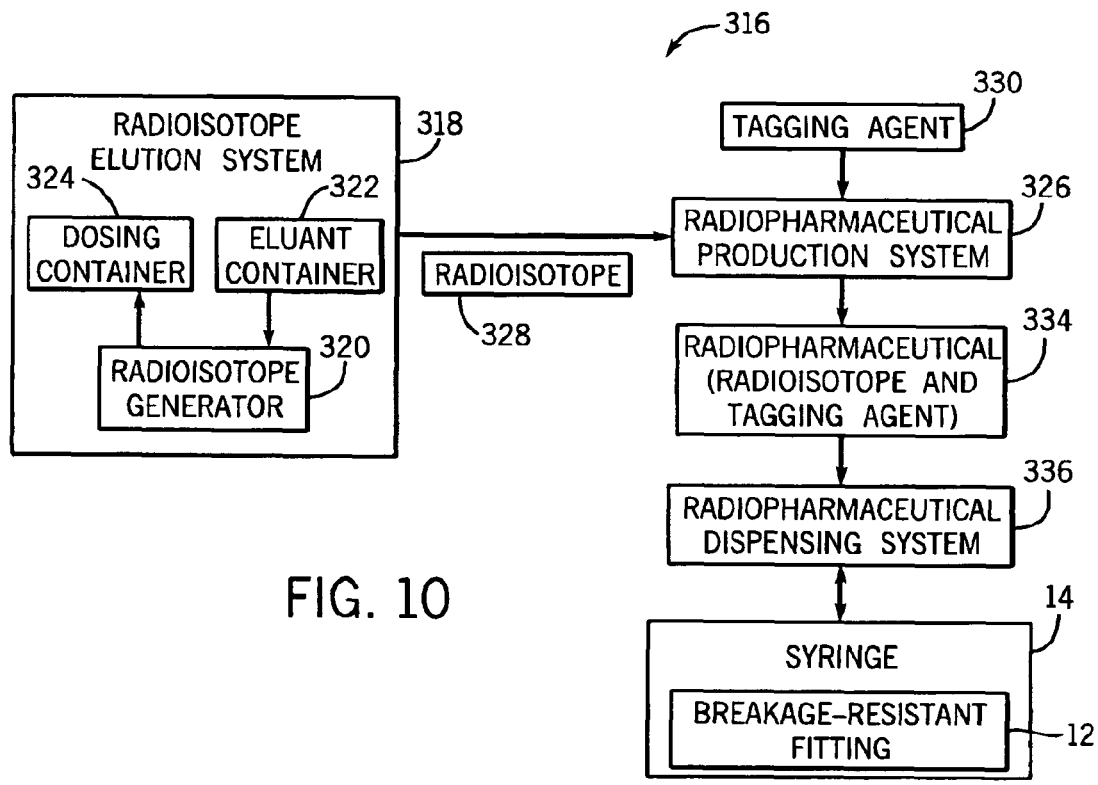
FIG. 10 is a block diagram illustrating an embodiment of a radiopharmacy or system utilizing one or more of the syringes having a breakage resistant fitting as illustrated in FIGS. 1-8.

FIG. 10 is a block diagram of an exemplary system 316 for providing a syringe 14 having a radiopharmaceutical disposed therein for use in a nuclear medicine application. Again, the syringe 14 may include the breakage resistant fitting 12 as discussed in detail above with reference to FIGS. 1-8. As illustrated, the system 316 includes a radioisotope elution system 318 having a radioisotope generator 320, an eluant supply container 322, and an eluate output container or dosing container 324. In certain embodiments, the eluate container 324 may be in vacuum, such that the pressure differential between the eluant supply container 322 and the eluate container 324 facilitates circulation of the eluant 32 through the radioisotope generator 320 and out through eluate conduit into the eluate container 324. As the eluant, e.g., a saline solution, circulates through the radioisotope generator 320, the circulating eluant generally washes out or elutes a radioisotope, e.g., Technetium-99m. For example, one embodiment of the radioisotope generator 320 includes a radiation shielded outer casing (e.g., lead shell) that encloses a radioactive parent, such as molybdenum-99, adsorbed to the surfaces of beads of alumina or a resin exchange column. Inside the radioisotope generator 320, the parent molybdenum-99 transforms, with a half-life of about 67 hours, into metastable technetium-99m. The daughter radioisotope, e.g., technetium-99m, is generally held less tightly than the parent radioisotope, e.g., molybdenum-99, within the radioisotope generator 320. Accordingly, the daughter radioisotope, e.g., technetium-99m, can be extracted or washed out with a suitable eluant, such as an oxidant-free physiologic saline solution. The eluate output from the radioisotope generator 320 into the eluate container 324 generally includes the eluant and the washed out or eluted radioisotope from within the radioisotope generator 320. Upon receiving the desired amount of eluate within the eluate output container 324, a valve may be closed to stop the eluant circulation and output of eluate. As discussed in further detail below, the extracted daughter radioisotope can then, if desired, be combined with a tagging agent to facilitate diagnosis or treatment of a patient (e.g., in a nuclear medicine facility).

The system 316 also includes a radiopharmaceutical production system 326, which functions to combine a radioisotope 328 (e.g., technetium-99m solution acquired through use of the radioisotope elution system 318) with a tagging agent 330. In some embodiments, this radiopharmaceutical production system 326 may refer to or include what are known in the art as "kits" (e.g., Technescan® kit for preparation of a diagnostic radiopharmaceutical). Again, the tagging agent may include a variety of substances that are attracted to or targeted for a particular portion (e.g., organ, tissue, tumor, cancer, etc.) of the patient. As a result, the radiopharmaceutical production system 326 produces or may be utilized to produce a radiopharmaceutical including the radioisotope 328 and the tagging agent 330, as indicated by block 334. The illustrated system 316 may also include a radiopharmaceutical dispensing system 336, which facilitates extraction of the radiopharmaceutical into a vial or syringe, such as the syringe 14 having the breakage resistant fitting 12 as discussed in detail above with reference to FIGS. 1-8. In certain embodiments, the various components and functions of the system 316 are disposed within a radiopharmacy, which prepares the syringe 14 of the radiopharmaceutical for use in a nuclear medicine application. For example, the syringe 14 may be prepared and delivered to a medical facility for use in diagnosis or treatment of a patient.

Figure 11:
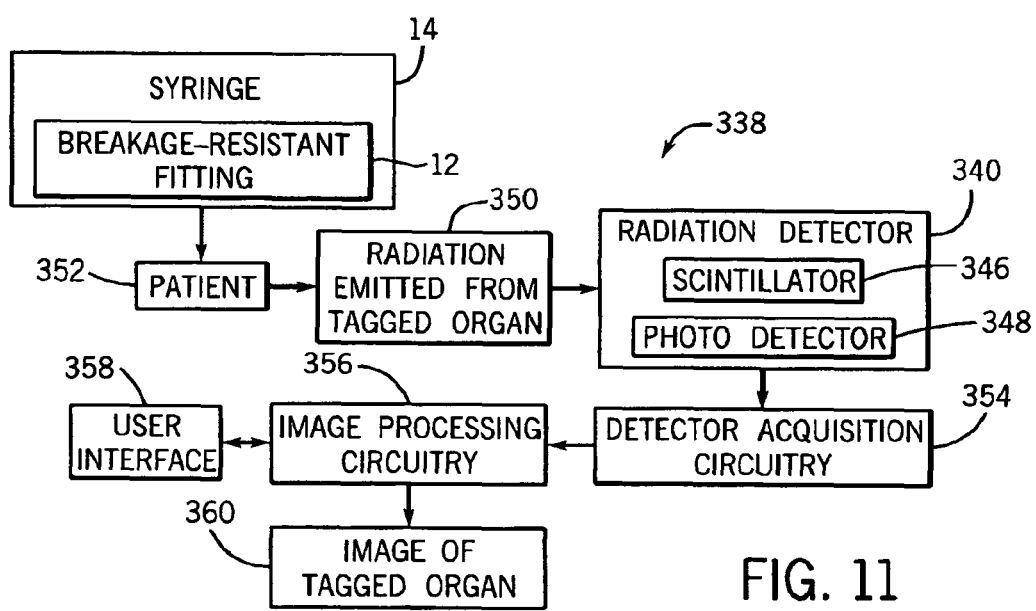
FIG. 11 is a block diagram illustrating an embodiment of a nuclear imaging system utilizing one or more of the syringes having a breakage resistant fitting as illustrated in FIGS. 1-8.

FIG. 11 is a block diagram of an exemplary nuclear medicine imaging system 338 utilizing the syringe 12 of radiopharmaceutical provided using the system 316 of FIG. 10. As illustrated, the nuclear medicine imagining system 338 includes a radiation detector 340 having a scintillator 346 and a photo detector 348. In response to radiation 350 emitted from a tagged organ within a patient 352, the scintillator 346 emits light that is sensed and converted to electronic signals by the photo detector 348. The imaging system 338 also can include a collimator to collimate the radiation 350 directed toward the radiation detector 340. The illustrated imaging system 338 also includes detector acquisition circuitry 354 and image processing circuitry 356. The detector acquisition circuitry 354 generally controls the acquisition of electronic signals from the radiation detector 340. The image processing circuitry 356 may be employed to process the electronic signals, execute examination protocols, and so forth. The illustrated imaging system 338 also includes a user interface 358 to facilitate user interaction with the image processing circuitry 356 and other components of the imaging system 338. As a result, the imaging system 338 produces an image 360 of the tagged organ within the patient 352. Again, the foregoing procedures and resulting image 360 directly benefit from the breakage resistant fitting 12 as illustrated and described with reference to FIGS. 1-8.

When introducing elements of the present invention or various embodiments thereof, the articles "a", "an", "the", and "said" are intended to mean that there are one or more of the elements. The terms "comprising", "including", and "having" are intended to be inclusive and mean that there may be additional elements other than the listed elements. Moreover, the use of "top", "bottom", "above", "below" and variations of these terms is made for convenience, but does not require any particular orientation of the components.

While the invention may be susceptible to various modifications and alternative forms, specific embodiments have been shown by way of example in the figures and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A connection comprising a luer fitting and a mating fitting that are each disposed about a centerline that extends in an axial dimension, wherein the mating fitting comprises a first projection, wherein the luer fitting comprises:
   a male luer comprising a tip;
   a luer collar disposed about and spaced from the male luer, wherein the luer collar further comprises an internal thread that extends toward but not to the male luer; and
   a receptacle between the male luer and the luer collar, wherein the receptacle comprises a base portion that comprises:
   a fulcrum that extends at least partially around a circumference of the male luer, wherein the fulcrum is spaced from the luer collar, and wherein the fulcrum is spaced further from the tip of the male luer than the internal thread in the axial dimension; and
   an expansion space between the fulcrum and the luer collar, wherein the first projection of the mating fitting is seated on the fulcrum, extends beyond the fulcrum into the expansion space, and is engaged by the internal thread, and wherein part of the first projection within the expansion space is spaced further from the tip of the male luer than the fulcrum in the axial dimension.

2. The connection of claim 1, wherein the male luer comprises an outer surface, and wherein the luer collar comprises an inner surface.

3. The connection of claim 2, wherein the outer surface of the male luer is spaced from the inner surface of the luer collar.

4. The connection of claim 2, wherein a perimeter of the fulcrum is spaced from the inner surface of the luer collar.

5. The connection of claim 4, wherein the expansion space extends from the perimeter of the fulcrum to the inner surface of the luer collar.

6. The connection of claim 1, wherein the expansion space extends from the fulcrum deeper into the receptacle in direction that is away from the tip of the male luer.

7. The connection of claim 1, wherein a bottom of the expansion space and the fulcrum are spaced in the axial dimension, with the bottom of the expansion space being spaced further from the tip of the male luer than the fulcrum in the axial dimension.

8. The connection of claim 1, wherein the fulcrum is spaced a first distance from the tip measured in the axial dimension, wherein a bottom of the expansion space is spaced a second distance from the tip measured in the axial dimension, and wherein the second distance is greater than the first distance.

9. The connection of claim 1, wherein the expansion space is disposed concentrically about the fulcrum.

10. The connection of claim 1, wherein the first projection of the mating fitting comprises a lug that in turn comprises a first portion that is seated on the fulcrum and a second portion that is deformed into the expansion space in a direction that is away from the tip of the male luer.

11. The connection of claim 1, wherein the first projection of the mating fitting is compressed between the internal thread and the fulcrum.

12. The connection of claim 1, wherein a perimeter of the first projection of the mating fitting is separated from an inner surface of the luer collar by a first portion of the expansion space, and wherein the part of the first projection, that is spaced further from the tip of the male luer than the fulcrum in the axial dimension, is within a second portion of the expansion space.

13. The connection of claim 1, wherein oppositely-directed forces are exerted on the first projection of the mating fitting by the fulcrum and the internal thread.

14. The connection of claim 1, wherein the first projection of the mating fitting curves into the expansion space proceeding from the fulcrum and in a direction that is away from the tip of the male luer.

15. The connection of claim 1, wherein a first portion of the expansion space exists between the first projection of the mating fitting and the luer collar, and wherein the first projection is deformed about the fulcrum into a second portion of the expansion space by contact with the internal thread of the luer collar.

16. A syringe system comprising a syringe and the connection of claim 1, wherein the syringe comprises the luer fitting.

17. The syringe system of claim 16, further comprising a fluid transmission system, wherein the fluid transmission system comprises the mating fitting.

18. The syringe system of claim 17, wherein the fluid transmission system further comprises tubing.

19. A connection, comprising:
    a luer fitting comprising:
        a male luer disposed about a centerline that extends in an axial dimension, wherein the male luer comprises a tip and an outer surface;
        a luer collar disposed about the male luer and comprising an inner surface that is spaced from the outer surface of the male luer in a radial dimension that is orthogonal to the axial dimension, wherein the inner surface comprises an internal thread;
        a base portion extending from the outer surface of the male luer to the inner surface of the luer collar and comprising first and second base portions that are offset from each other in the axial dimension, wherein the second base portion is positioned further from the centerline than the first base portion, wherein the second base portion is positioned further from the tip of the male luer than the first base portion in the axial dimension, and wherein the second base portion is spaced further from the tip of the male luer than an entirety of the internal thread in the axial dimension; and
    a mating fitting engaged with the luer fitting, wherein a first portion the mating fitting is seated on the first base portion and extends beyond the first base portion toward, but not to, the second base portion by the internal thread of the luer collar deforming the first portion about the first base portion.

20. The connection of claim 19, wherein the second base portion is disposed between the inner surface of the luer collar and the first base portion in the radial dimension.

21. The connection of claim 19, wherein the first base portion extends from the outer surface of the male luer, and wherein a perimeter of the first base portion is spaced from the inner surface of the luer collar in the radial dimension.

22. The connection of claim 19, wherein the internal thread of the luer collar engages with the first portion of the mating fitting such that the mating fitting is compressed between the internal thread and the first base portion.

23. The connection of claim 22, wherein a perimeter of the first portion of the mating fitting is spaced from each of the inner surface of the luer collar and the second base portion of the luer fitting.

24. A syringe system comprising a syringe and the connection of claim 19, wherein the syringe comprises the luer fitting.

25. The syringe system of claim 24, further comprising a fluid transmission system, wherein the fluid transmission system comprises the mating fitting.

26. The syringe system of claim 25, wherein the fluid transmission system further comprises tubing.

* * * * *

UNITED STATES PATENT AND TRADEMARK OFFICE
CERTIFICATE OF CORRECTION

| | |
|---|---|
| PATENT NO. | : 8,038,182 B2 |
| APPLICATION NO. | : 12/374059 |
| DATED | : October 18, 2011 |
| INVENTOR(S) | : Munehito Kurimoto et al. |

It is certified that error appears in the above-identified patent and that said Letters Patent is hereby corrected as shown below:

At Column 13, line 7, delete "fulcum" and insert therefore --fulcrum--.

Signed and Sealed this
Twenty-ninth Day of November, 2011

David J. Kappos
*Director of the United States Patent and Trademark Office*